United States Patent [19]

Liu

[11] Patent Number: 5,155,111
[45] Date of Patent: Oct. 13, 1992

[54] DDB AS AN AGENT AGAINST BEL-7402 HUMAN HEPATOCARCINOMA

[75] Inventor: Geng-Tao Liu, Beijing, China

[73] Assignee: Institute of Materia Medica, Beijing, China

[21] Appl. No.: 518,271

[22] Filed: May 7, 1990

Related U.S. Application Data

[63] Continuation of Ser. No. 297,622, Jan. 17, 1989, abandoned.

[51] Int. Cl.⁵ .................... H61K 31/52; H61K 31/36
[52] U.S. Cl. ..................................... 514/262; 514/464
[58] Field of Search ................................ 514/262, 464

[56] References Cited

PUBLICATIONS

Chemical Abstracts 104:109612t (1986).
Chemical Abstracts 108:81931c (1988).

*Primary Examiner*—Jerome D. Goldberg
*Attorney, Agent, or Firm*—Armstrong & Kubvocik

[57] ABSTRACT

Dimethyl-4,4'-dimethoxy-5,6,5',6'-dimethylenedioxybiphenyl-2,2'-dicarboxylate (DDB), a synthetic analogue of Schizandrin C, is a useful chemotherapeutic agent for the treatment of BEL-7402 human hepatocarcinoma when used in combination with 6-mercaptopurine.

3 Claims, 12 Drawing Sheets

MITOTIC INDEX OF ASCITIC HEPATOMA
TREATED WITH DDB AT DIFFERENT CONCENTRATIONS
n=6  P<0.01, *P<0.001

EFFECT OF DDB ON $^3$H-TdR INCORPORATION INTO DNA OF REGENERATING HEPATOCYTES CULTURED IN VITRO

EFFECT OF DDB ON $^3$H-Leucine INCORPORATION INTO PROTEIN OF REGENERATING HEPATOCYTES CULTURED IN VITRO

DDB AS AN AGENT AGAINST BEL-7402 HUMAN HEPATOCARCINOMA

This application is a continuation of application Ser. No. 297,622, filed Jan. 17, 1989, now abandoned.

BACKGROUND OF THE INVENTION

1. Field of the Invention

This invention relates to the use of dimethyl-4,4'-dialkoxy-5,6,5',6'-dimethylenedioxybiphenyl-2,2'-dicarboxylate, and particularly the dimethoxy homologue, (DDB), as a therapeutic agents, for the treatment of BEL-7402 human hepatocarcinoma, and to the use of these compounds in conjunction with other chemotherapeutic agents in the control of BEL-7402 human heptocarcinoma.

2. Background

DDB is a synthetic analogue of Schizandrin C, a physiologically active compound which can be isolated from *Fructus Schizandrae chinensis*, a traditional medicinal plant. Extracts of this plant have been used as a traditional Chinese tonic and have been shown to be useful in the treatment of chronic viral hepatitis and also for the treatment of liver injuries resulting from exposure to chemical toxins such as carbon tetrachloride, D-galactosamine and thioacetamide.

Treatment of patients with a chronic viral hepatitis B with DDB tablets has been shown to control the increase in serum glutamine pyruvate transaminase (SGPT), bilirubin and alpha-fetal protein, traditional indices of abnormal liver function, and has also proved to be effective in the control of such symptoms of hepatitis as anorexia, pain and flatulation. Since 1981, DDB has been the treatment of choice in the People's Republic of China for chronic hepatitis, particularly viral hepatitis B, as well as for drug-induced liver injuries.

BRIEF SUMMARY OF THE INVENTION

DDB and homologues there of have now been found to be useful as a chemotherapeutic agent to control the growth of certain neoplasia, including certain malignant neoplasia, both in vivo and in vitro. DDB prolongs the survival time of mice in which ascitic hepatoma cells have been implanted and has been shown to reduce the increase in the weight of solid lung carcinoma tumors implanted in mice. In vitro studies using cultured murine ascitic hepatoma cells have shown DDB to inhibit syntheses of DNA, RNA and proteins in neoplastic cells. Of particular significance is the fact that the inhibition of DNA and protein syntheses in cultured cells appears to be limited to neoplastic tissue and essentially no inhibition of these processes has been found in hepatocytes of liver cells obtained from partially hepatectomized rodents.

In addition to a primary effect in the prevention of growth of certain neoplastic tissue, DDB is also indicated to have utility when used in combination with other proved chemotherapeutic agents such as methotrexate and 6-mercaptopurine which, in pharmacological dosages, frequently exhibit cirrhotic side effects or other severe dosage-related limitations in use.

DETAILED DESCRIPTION OF THE INVENTION

Dimethyl-4,4'-dialkoxy-5,6,5',6'-dimethylenedioxybiphenyl-2,2'-dicarboxylate has the structural formula wherein R is lower alkyl.

The 4,4'-dimethoxy homologue was first synthesized by Xie et al., *Acta Pharm. Sinica*, 16, 306 (1981), Yaoxue Xuebao 17, 23 (1982). The racemic mixture is resolvable as reported Zhan et al., *Kexue Tongbao* 32 (1), 72 (1987). The compound has been shown to be effective treatment for liver disease in mice, as reported by Liu et al., *Chem.-Biol. Interactions*, 41, 39 (1982), and is also used for the treatment of viral hepatitis B and other drug-induced hepatic diseases in man in the People's Republic of China.

Dimethyl-4,4'-dimethoxy-5,6,5'6'-dimethylenedioxybiphenyl-2,2'-dicarboxylate (DDB) was an important intermediate used for the synthesis of Schizandrin C analogues.

The preferred method of synthesis of DDB is as follows:

DDB was synthesized from gallic acid by esterification, monomethylation, formation of the methylenedioxy derivative, bromination and the Ullmann reaction successively.

By using the mixed bromo compounds, separated from the mother liquid, as the starting material for an Ullmann reaction, the isomer dimethyl-6,6'-dimethoxy-4,5,4',5'-dimethylenedioxybiphenyl-2,2'-dicarboxylate (DDB) was obtained, which was separated by column chromatography on silica gel. DDB exhibits two crystalline forms with m.p.'s 158°–160° C. and 179°–181° C., both of which are effective in lowering the elevated SGPT level.

DDB, when administered for the treatment of liver diseases, may be administered in the form of a pilule or, less effectively, in a tableted form.

It has now been discovered that DDB is useful in controlling the growth of certain malignant cells in vivo and in vitro. This anti-tumor activity is demonstrated by its inhibitory effects on the growth of murine ascitic hepatoma cells and Lewis lung carcinoma cells implanted in mice; on the synthesis of DNA, RNA and proteins, and on cell proliferation in murine ascitic hepatoma cells in culture; on DNA synthesis and cell proliferation using BEL-7402 human hepatocarcinoma cell lines in culture; and by the enhanced effects on the inhibition of DNA synthesis and cell proliferation of murine ascitic hepatoma cells when treated with DDB and other proven anti-cancer chemotherapeutic agents.

Neoplastic tissues, particularly malignant neoplastic tissues, are characterized by rapid and essentially undifferentiated cell proliferation. Metastatic cells are also capable of systemic transportation and redeposition and are readily transplanted. In addition, tumor cell lines can be cultured in vitro for an indefinite period of time. One method for testing the efficacy of chemotherapeutic agents is to implant cultured tumor cell lines into host animals, typically mammals, and to treat the host animals with the putative therapeutic agent.

Murine ascitic hepatoma cells, obtained originally from an inducible hepatoma and then transplanted into H22 mice by Russian scientists, may be implanted into healthy mice and allowed to grow therein. When murine ascitic hepatoma cells are implanted in Kumin mice weighing approximately 20 g, the survival time of the host is typically less than 60 days. When these mice are treated with 600 mg/kg/day of DDB, suspended in 0.2% sodium carboxymethyl cellulose (CMC-Na) by intubation, the survival rate is approximately 80% over a period of 60 days. These results indicate that DDB, or a metabolite thereof, achieves systemic distribution and has anti-tumor effects in vivo.

Lewis murine lung carcinoma is a solid tumor obtained from C57-BL/6 mice. When tumor cells are inoculated subcutaneously in 20 g Kumin strain mice, tumor growth continues in the mice. It has been found that treatment with DDB, by intubation, using 0.2% CMC-Na as the vehicle, results in inhibition of tumor weight increase without substantial change in the increase in body weight of the mice. The $ED_{50}$ has been calculated to be about 640 mg/kg/day. Inhibition of tumor growth in the absence of inhibition of total body weight gain indicates a high selectivity of DDB for the tumor cells and low toxicity of the therapeutic agent.

A definitive characteristic of malignant neoplasia is rapid cell proliferation, in vivo and in vitro. Inhibition of cell proliferation in the presence of a putative anti-tumor therapeutic agent in vitro is strongly indicative of the efficacy and potency of a chemotherapeutic agent in vivo. For example, see Sun Yan and Han Rul, *Recent Advances in Cancer Chemotherapy*, pp 44–55, Shandong Acad. Press., Hunan, PRC, 1987. When DDB is added to a cell culture medium in which murine ascitic hepatoma cells are conventionally grown, cellular proliferation is inhibited in a dose dependent manner.

Cellular proliferation requires the synthesis of new DNA to be incorporated into the daughter cells during mitosis. Chemotherapeutic agents which directly inhibit mitosis are particularly valuable because inhibition o mitosis is indicative of a broad spectrum of utility in the treatment of neoplastic diseases (see Sun Yan et al. supra). An indication of the mode of action of a chemotherapeutic agent which inhibits DNA synthesis is the measurement of the uptake of a tritiated nucleoside by cells in culture. When DDB is added to a culture medium, followed by addition of a tritiated nucleoside such as thymidine, uptake of the tritiated thymidine into the nuclear DNA has been shown to be inhibited, in a dose dependent manner, in both murine ascitic hepatoma cells and in BEL-7402 human hepatocarcinoma cells.

The rate of growth of individual tumor cells is dependent, at least in part, upon the production of RNA in the cell. RNA production can be measured by the uptake of tritiated uridine in a cultured cell. When murine ascitic hepatoma cells are pre-incubated with various concentrations of DDB and when tritiated uridine is then added to the culture medium, uptake of uridine is inhibited. The inhibition is not classically dose dependent in the sense that a linear dose response curve is not generated and the degree of inhibition is significantly less than the inhibition observed in the uptake of tritiated thymidine into nuclear DNA.

Protein synthesis in a growing cell can be measured by the uptake of tritiated amino acids. When murine ascitic hepatoma cells were pre-incubated with various concentrations of DDB and tritiated leucine was subsequently added to the culture media, uptake of the tritiated leucine, corresponding to the rate of protein synthesis, was inhibited in a dose dependent manner.

An alternative measurement of the rate of growth of tissue is a determination of cell-cycle times. Of particular significance in determination of the rate of cell division in neoplastic cells is the determination of the "M-phase" which begins with mitosis and terminates with cytokinesis. During the early portion of the M-phase, the replicated chromosomes condense and are easily identified by light microscopy. The mitotic index is the fraction of cells containing condensed chromosomes at any one time (after applying a slight correction factor based upon the ratio of new to old cells). When murine ascitic hepatoma cells are incubated for 24 hours in media containing various concentrations of DDB, the mitotic index decreases in a dose dependent manner, indicating that the rate of tumor growth is inhibited by DDB.

The utility of a chemotherapeutic agent in the treatment of malignant tumors is limited by the toxicity of the agent to differentiated or "normal" tissues. Agents which are universally cytotoxic must be concentrated within the target tissues or the toxic side-effects on target organs and other organs will be unacceptable. The results reported supra strongly suggest that DDB functions by interrupting cellular division to prevent growth of the tumor. The safety, and ultimately, the efficacy, of DDB as a systemically distributed chemotherapeutic agent requires that DDB not significantly interfere with the normal proliferation of non-neoplastic tissues.

When hepatocytes isolated from partially hepatectomized rats were cultured in the presence of various levels of DDB, corresponding to the concentrations shown to have a dose dependent inhibitory effect on hepatoma cells, measurement of tritiated thymidine uptake, tritiated uridine uptake and tritiated leucine uptake in the regenerated hepatocytes is essentially indistinguishable from untreated or control cells.

Mercaptopurine (6-MP) is an analogue of hypoxanthine in which the keto oxygen at C-6 of the purine ring is replaced by a sulfur atom. The compound is an established clinical agent for treatment of human leukemias. 6-MP is converted enzymatically to 6-thioGMP, the presence of which inhibits purine ring biosynthesis and nucleotide interconversion. Adults treated with therapeutic doses of 6-MP develop jaundice in approximately one-third of the patients treated.

When mice are implanted with murine ascitic hepatoma cells and administered 6-MP intraperitoneally, all of the treated mice were dead within 42 days. Identical mice treated with the same dosage of 6-MP and with DDB (300 mg/kg/day, p.o.) had a 60% survival rate over the same period of time.

When murine ascitic hepatoma cells in culture were treated with DDB alone, followed by incubation in tritiated thymidine, an approximately 70% inhibition of thymidine uptake in DNA was observed. When a equivalent concentration of 6-MP was substituted for DDB, approximately 56% inhibition in the uptake of tritiated thymidine was observed. When equal amounts of DDB and 6-MP, each amount corresponding to the amount described above, the inhibition was approximately 84%. Concurrent treatment with 6-MP and DDB is indicated to be more potent than treatment with an individual agent and the hepato-protective effects of DDB may be expected to minimize cirrhotic complications which frequently attend administration of 6-MP exclusively.

Methotrexate is a folic acid analogue with a high affinity for dihydrofolate reductase. Administration of methotrexate interrupts the synthesis of both DNA and RNA. Serious side-effects from methotrexate treatment include leukopenia and "rescue" with leucovorin is usually required when therapeutic doses are administered. Other side-effects include thrombocytopenia, which may require platelet transfusions.

Coadministration of DDB and methotrexate has been shown, in cell cultures, to significantly decrease tritiated thymidine incorporation into the DNA of murine ascitic hepatoma cells when compared to treatment with DDB or methotrexate alone.

The present invention also relates to pharmaceutical preparations containing DDB. The pharmacologically effective compounds of this invention can be processed by conventional methods of pharmacy including pharmaceutical preparations for oral or parenteral administration to mammals including humans. Suitable excipients are pharmaceutically acceptable organic and inorganic carrier substances suitable for parenteral, and enteral application, which do not deleteriously react with the active compound. Suitable carriers include, but are not necessarily limited to, water, saline solutions, alcohols, gum arabic, vegetable oils, polyethylene glycols, gelatin, saccharides, magnesium stearate, talc, silicic acid, paraffins, fatty acid monoglycerides and diglycerides, pentaerythritol, fatty acid esters, hydroxymethylcellulose and its salts, polyvinyl pyrrolidone etc. The pharmaceutical preparations may be sterilized and, if desired, mixed with auxiliary agents such as lubricants, preservatives, stabilizers, wetting agents, emulsifiers, buffers, coloring and/or flavoring compositions which do not deleteriously react with the active compounds. Particularly suitable are compositions designed for enteral administration, in the form of tablets, pilules, cachets and capsules. Compatible, non-toxic diluents such as flour, kaolin, powdered rice may be used. Binders such as gum arabic, tragacanth, refined sugar, gelatin, starch, and carboxymethyl cellulose are suitable for solid preparations. Excipients such as glucose, glycerin, acacia mucilage and syrups may be added. Tablet forms may also include disintegrators such as certain celluloses, yeasts, and powdered laminaria. Suppositories having a waxy base are also suitable. Sustained release formulations having one or more degradable coatings and microencapsulation are also envisioned. The standard formularies such as the U.S. Pharmacopoeia, National Formulary and British Pharmaceutical Codex may be used as a guide in formulating suitable preparations. The methods of manufacture should follow those described in standard reference texts such as "Remington's Practice of Pharmacy". The most preferred form for administration is the pilule, which is described in Japanese published patent application Sho 60-209582.

The compositions of this invention may be dispensed in unit dosage form comprising 30 to 150 mg, preferably 45 to 60 mg, of active ingredient in a pharmaceutically acceptable carrier. Suitable daily dosages for humans are 1.25 to 6.50 mg/kg/day, subject to the clinical experience of the administering physician and to the treatment regimen, which may include the use of additional chemotherapeutic agents, radiation, etc.

The utility of the above-described invention is further illustrated by reference to the following examples. These examples are representative only and are not limitative to the invention disclosed. Certain modifications, within the scope of these teachings, will be apparent to those skilled in the art.

REFERENCE EXAMPLE 1

Synthesis of dimethyl-4,4'-dimethoxy-5,6,5',6'-bismethylenedioxybiphenyl-2,2'-dicarbonate (DDB)

1. Methyl Gallate

Twenty 20 ml of concentrated sulfuric acid was added dropwise to a solution of 200 g of gallic acid in 600 ml of methanol at room temperature with stirring for 6–8 hours. After approximately ⅔ of the methanol was removed, the residue was cooled to 10° C., poured into 1.2 kg of water and allowed to stand overnight. The white precipitate which formed was filtered and washed with water to give 178 g of product methyl gallate, m.p. 200°–204° C. (yield 82%).

2. Methyl-3-methoxy-4,5-dihydroxybenzoate

To a mixture prepared by dissolving 25 g methyl gallate in aqueous borax solution (70 g borax in 1.5 l water) was separately added 60 ml dimethyl sulfate and aqueous NaOH solution (26 g NaOH in 100 ml water) through a dropping funnel, with stirring, at room temperature for a period of 6 hours. During addition, the pH of the reaction mixture was maintained at 8–9. After addition, the mixture was allowed to stand overnight and acidified with concentrated $H_2SO_4$ to pH 3 and extracted with ethyl acetate. The solvent was evaporated and the residue was washed with toluene and water to obtain 21.3 g mono-methoxy ether, m.p. 111°–113° C. (yield 79%).

3. Methyl-3,4-dihydroxy-5-methoxy benzoate

A mixture of 14.0 kg mono-methoxy ether, 5.7 g diiodomethane and 25 g anhydrous potassium carbonate in 150 ml acetate was refluxed for 40 hours. After cooling, the reaction mixture was filtered and the solvent was evaporated and the residue was allowed to stand overnight. The residue then was washed with water and 10% alcohol 3 to 4 times to yield 4.2 g of the title compound in the form of a white solid, m.p. 89°–90° C. (recrystalization from EtOH, yield 69%).

4. Methyl-2-bromo-3,4-bismethylenedioxy-5-methoxybenzoate

A solution of 16.8 g bromine in 60 ml glacial acetic acid was added dropwise to a solution of 22 g methylenedioxy derivative obtained above in 130 ml glacial acetic acid was stirred at 12°–14° C. for 3 hours. After addition of bromine, the mixture was stirred for an additional 2 hours. Then the reaction mixture was poured into ice water, and the precipitated solid was filtered and washed with water until the washing solution was neutral to yield 22 g crude product. Recrystallization from EtOH yielded 19 g bromo-compound, m.p. 102°–104° C. (yield 64%).

5. Dimethyl-4,4'-dimethoxy-5,6,5',6'-bismethylenedioxy-2,2'-dicarboxylate (DDB)

A mixture of 50 g of the bromo compound (4) obtained above and 34 g copper powder in 160 ml DMF was refluxed and stirred for 2 hours. After removal of DMF, the residue was extracted with benzene and methylene chloride (1:1) and evaporated to yield a white crystalline solid, which was recrystallized from methanol: chloroform (1:3) to yield 31.4 g DDB, m.p. 158°–160° C. or 178°–180° C. (due to the different crystalline forms), yield 87%.

EXAMPLE 1

Figure 1:
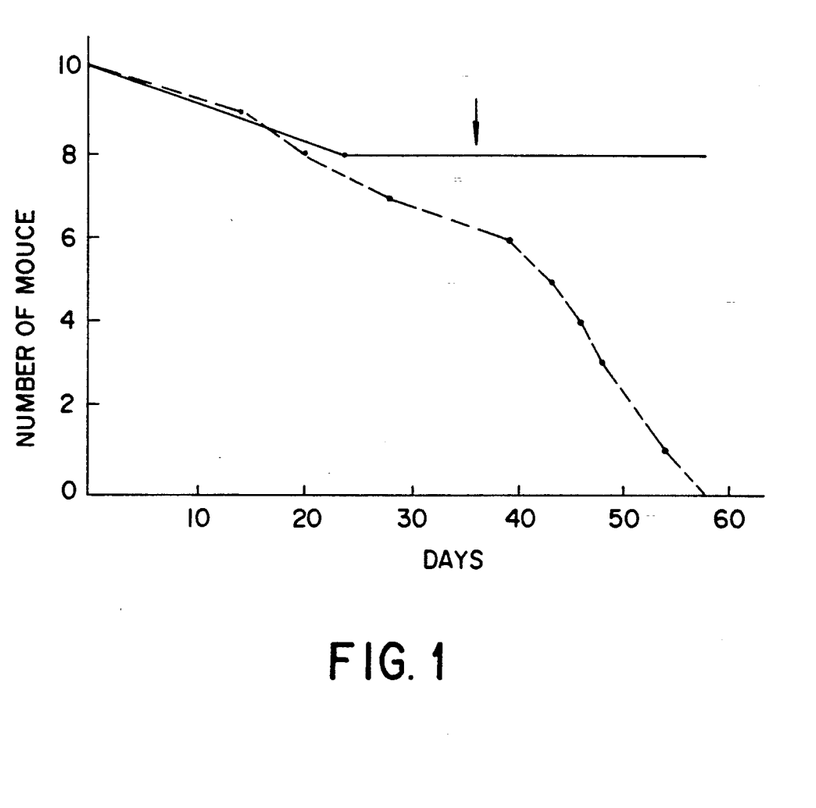
FIG. 1 is a plot of survival times for mice having implanted murine ascitic hepatoma cells with and without treatment with DDB.

Twenty male Kumin strain mice, weighing between 18 and 22 g, were inoculated i.p. with equal aliquots of suspended murine ascitic hepatoma cells obtained from Kumin mice. The mice were maintained on a diet of laboratory chow prepared by the Institute of Experimental Animals, CAMS, and water ad lib. One day after inoculation, the mice were divided into 2 groups. To 1 group was administered 300 mg/kg of DDB suspended in 0.2% CMC-Na (10 ml/kg) twice daily, by intubation. The control group was administered the same volume of vehicle. Treatment was terminated on the 38th day. After 58 days from the date of inoculation, all mice in the control group had died, whereas 8 of the 10 mice treated with DDB survived. FIG. 1 is a graph showing the number of mice surviving in each group over a period of 58 days.

EXAMPLE 2

Male Kumin strain mice, as used in Example 1, were inoculated subcutaneously with 0.1 ml aliquots of homogenates of Lewis lung carcinoma cells obtained from C57-BL/6 mice and divided into four groups. The animals were fed a diet of laboratory chow and water ad lib. To 3 of the groups, DDB was administered by intubation in 0.2% CMC-Na. The dosages were 75, 150 and 300 mg/kg/day in an equal volume. Control mice were administered the same volume of vehicle. DDB was administered for 9 days ad, on the 10th day, each mouse was weighed and then sacrificed. Tumors were excised and weighed individually. The results are indicated in Table 1.

TABLE 1

Effect of DDB on Lewis Lung Carcinoma in Mice
$\bar{X} \pm$ S.D.

| Group | Dose mg/kg × days | n | Tumor wt. g | Inhibition % | Body wt. change g |
|---|---|---|---|---|---|
| Control | | 11 | 2.06 ± 0.64 | | +4.0 |
| DDB | 75 × 9 | 11 | 1.65 ± 0.43 | 19.9 | +3.8 |
| | 150 × 9 | 11 | 1.57 ± 0.52 | 23.8 | +3.5 |
| | 300 × 9 | 12 | 1.17 ± 0.33 | 43.2* | +3.8 |

*p < 0.001

EXAMPLE 3

Figure 2:
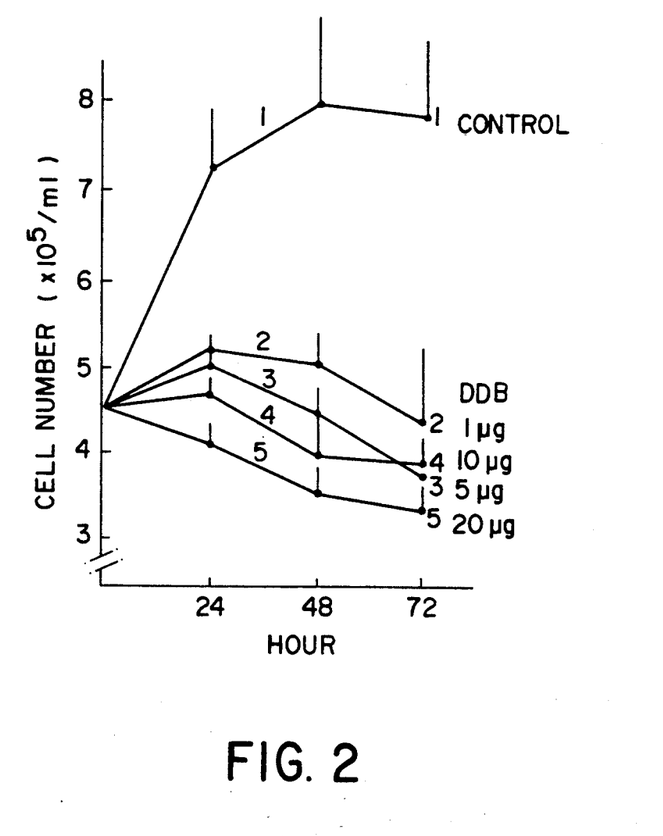
FIG. 2 is a plot of cell proliferation for murine ascitic hepatoma cells in vitro at various concentrations of DDB.

Suspensions of murine ascitic hepatoma cells at a concentration of $1 \times 10^5$ cells/ml were cultured in medium, RPMI-1640 to which was added 10 μl of DMSO containing 1, 5, 10 and 20 μg of DDB. To the control was added 10 μl of DMSO only. The culture 3 were was incubated in a $CO_2$ incubator and 6 aliquots were withdrawn from each culture at 24, 48 and 72 hours and counted under a microscope at 40× magnification. The results are shown in FIG. 2. The difference between the control and DDB groups is statistically significant (p<0.01).

EXAMPLE 4

Figure 3:
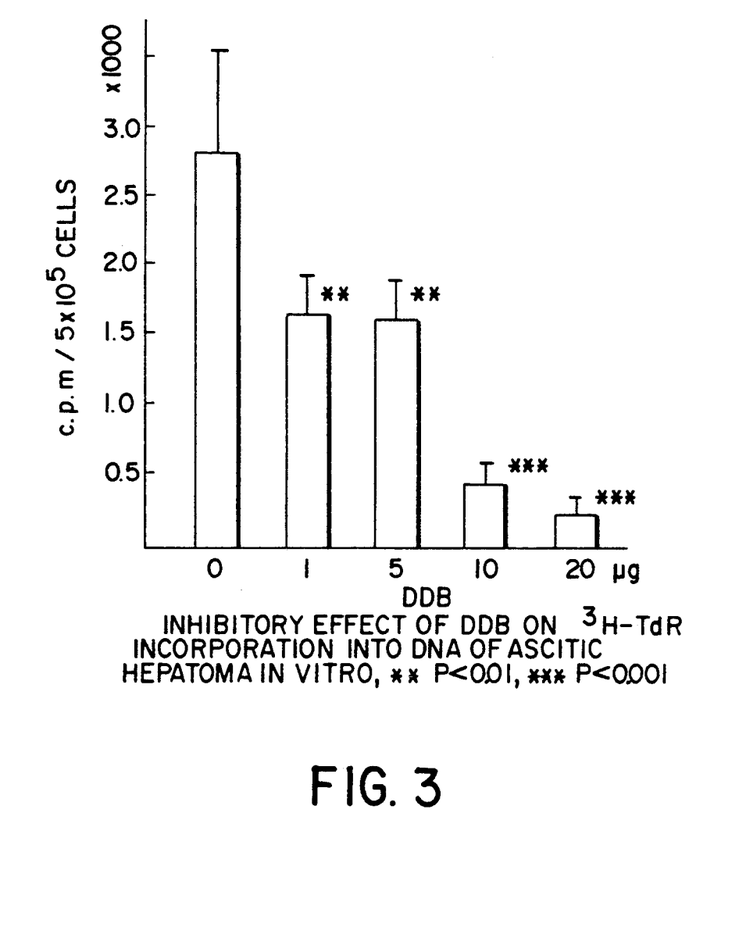
FIG. 3 is a graph showing the incorporation of tritiated thymidine in cultured murine ascitic hepatoma cells in the presence of various concentrations of DDB.

Murine ascitic hepatoma cells were suspended at a density of $5 \times 10^5$ cells/ml in RPMI-1640 and 1 ml of cell suspension was added to Petri dishes and incubated for 24 hours with 0, 1, 5, 10 and 20 μg of DDB in 10 ml of DMSO. Tritiated thymidine (0.5 μci) was added to each dish and incubation continued for 4 additional hours. 0.1 ml 1% Triton X-100 was added to lyse the cells. 2 ml 10% trichloroacetic acid (TCA) was added. After centrifugation, 1 ml of 5% TCA was added to isolate nucleic acid. 0.2 ml of the liquid was added to Bray's liquid scintillation cocktail, and the radioactivity was counted on Beckman LS-9800 Scintillation Counter. The results are shown in FIG. 3.

EXAMPLE 5

Figure 4:
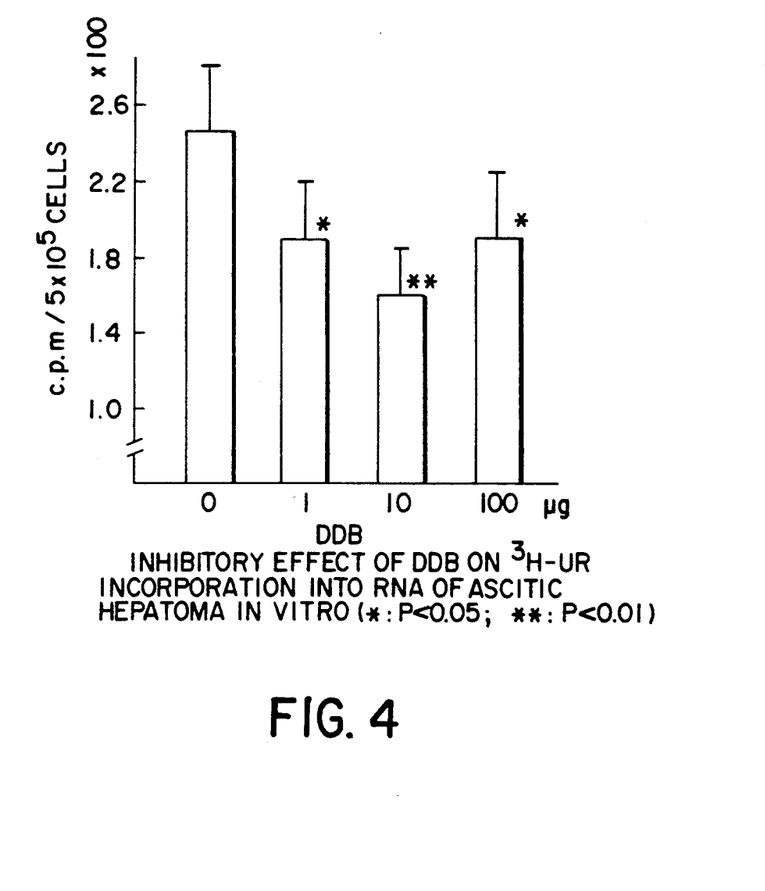
FIG. 4 is a graph of tritiated uridine incorporation in the RNA of cultured murine ascitic hepatoma cells at various concentrations of DDB.

Murine ascitic hepatoma cells ($5 \times 10^5$ cells/ml) were pre-incubated for 24 hours in 1 ml RPMI-1640 medium in a 5% $CO_2$ incubator with 0, 1, 10 and 100 μg/ml of DDB in DMSO as described in Example 4. Tritiated uridine, 0.5 μci was added to the media and incubation continued for 4 additional hours. The cells were treated in the same manner as Example 4 and the incorporated tritiated uridine was measured as described. The results are shown in FIG. 4.

EXAMPLE 6

Figure 5:
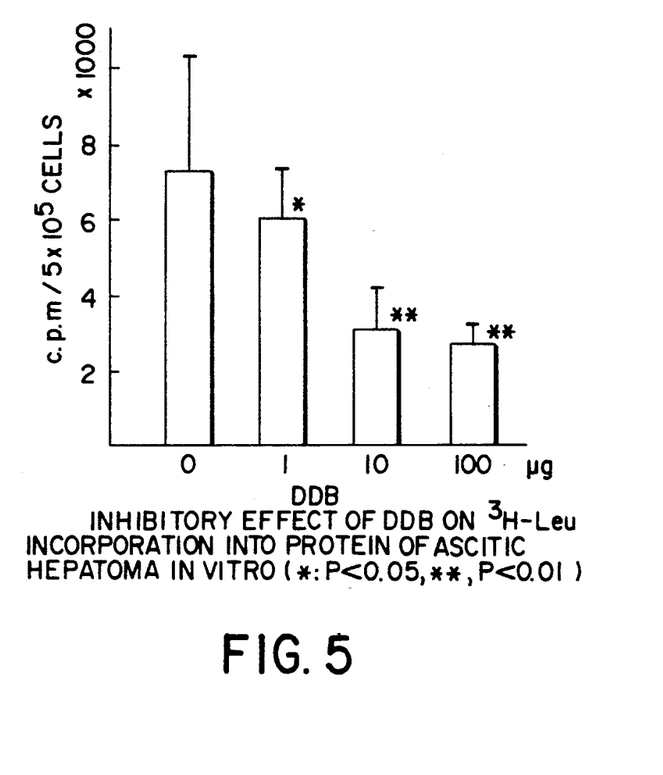
FIG. 5 is a graph of tritiated leucine incorporation in the protein of cultured murine ascitic hepatoma cells at various concentrations of DDB.

Murine ascitic hepatoma cells ($5 \times 10^5$ cells/ml) were incubated for 24 hours in 1 ml RPMI-1640 medium in a 5% $CO_2$ incubator in the presence of 0, 1, 10 and 100 μg/ml of DDB in DMSO as described in Example 4. Tritiated leucine, 0.5 μci was added to each sample and incubated for an additional 4 hours. The sample was treated as described in Example 4. The protein precipitates were dissolved in 0.5 ml of 0.4N NaOH and 0.4 ml of the protein solution was added to the scintillation cocktail and the radioactivity determination. The results are shown in FIG. 5.

EXAMPLE 7

Figure 6:
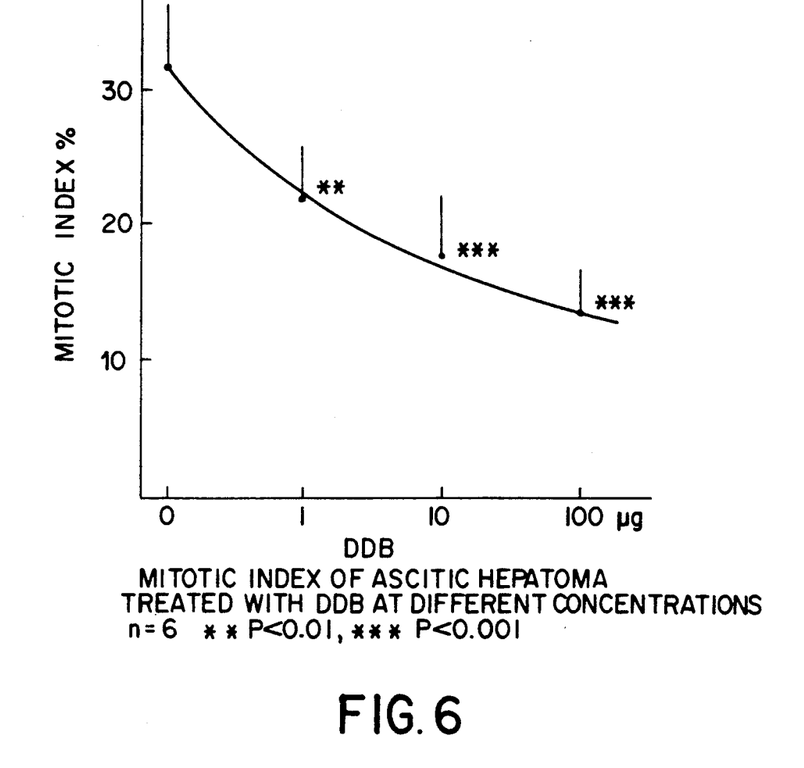
FIG. 6 is a plot of the mitotic index of cultured murine ascitic hepatoma cells treated with various concentrations of DDB.

Murine ascitic hepatoma cells at an initial concentration of $5 \times 10^5$ cells/ml were grown in 1 ml RPMI-1640 medium in a 5% $CO_2$ incubator for 24 hours in the presence of 0, 1, 10 and 100 μg/ml of DDB in DMSO. Upon termination of incubation, the suspensions were centrifuged at $500 \times G$ for 5 minutes. Drops of the cell suspension were withdrawn from the cell layer and stained with Wrights-Glemsa stain. Random groups of 500 cells were observed under a microscope at $400 \times$ and the number of cells in M-phase in each group were counted. The results are shown in FIG. 6.

EXAMPLE 8

Figure 7:
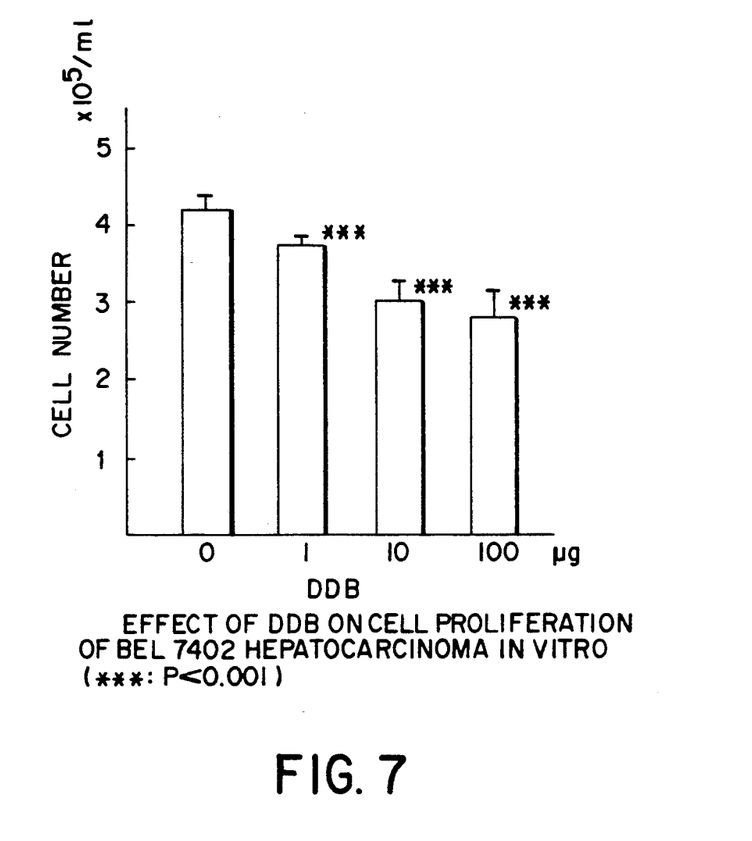
FIG. 7 is a graph showing cell proliferation of cultured BEL-7402 human hepatocarcinoma cells in the presence of various concentrations of DDB.

BEL-7402 human hepatocarcinoma tumor cells obtained from all culture lines were cultured in RPMI-1640 medium in Petri dishes at an initial concentration of $5 \times 10^5$ cells/ml to which had been added 10 μl of DMSO containing 0, 1, 10 and 100 μg of DDB. Drops from the cell cultures were withdrawn and counted under a microscope. The results are shown in FIG. 7. The minimum effective dose was calculated to be 1 μg DDB/ml medium.

EXAMPLE 9

Figure 8:
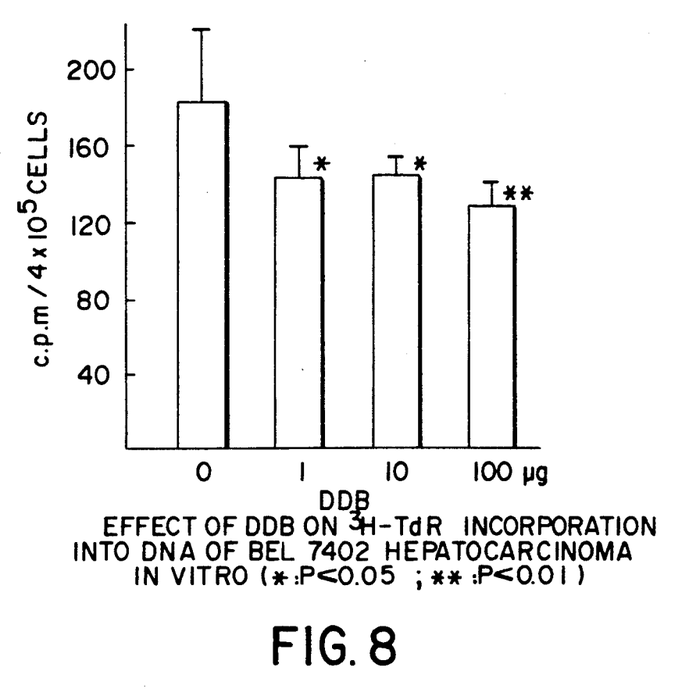
FIG. 8 is a graph of tritiated thymidine uptake in the DNA of cultured BEL-7402 human hepatocarcinoma cells at various concentrations of DDB.

BEL-7402 human hepatocarcinoma cells were cultured as described in Example 7. After 24 hours, 10 μl of tritiated thymidine, 0.5 μci was added to each culture and the uptake of thymidine measured as described in Example 4. The results are shown in FIG. 8.

EXAMPLE 10

Figure 9:
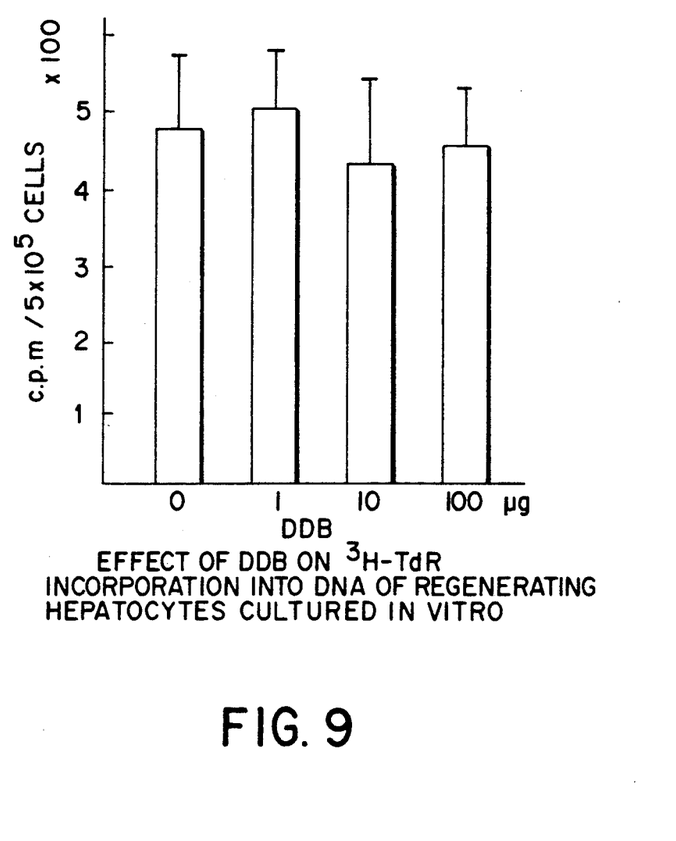
FIG. 9 is a graph of tritiated thymidine incorporation in the DNA of cultured regenerated rat hepatocytes at various concentrations of DDB.

Male Wistar rats weighing approximately 150 g were partially hepatectomized, approximately 70% of the liver being removed. The abdomens were sutured and the animals were maintained for 5 days on a diet of laboratory chow and water ad lib. The animals were sacrificed and the livers excised, perfused with collagenase solution and the hepatocytes isolated by the method of Seglen, P.O., *Methods Cell Biol.*, 13, 29 (1976). The hepatocytes were diluted to $5 \times 10^5$ cells/ml in RPMI-1640 medium and incubated with 0, 1, 10 and 100 μg of DDB in 10 μl of DMSO. After 24 hours, 0.5 μci of tritiated thymidine in 10 μl of normal saline was added to the culture medium and the suspension was incubated for an additional 4 hours and the cells were treated as in Example 4. The results are shown in FIG. 9.

EXAMPLE 11

Figure 10:
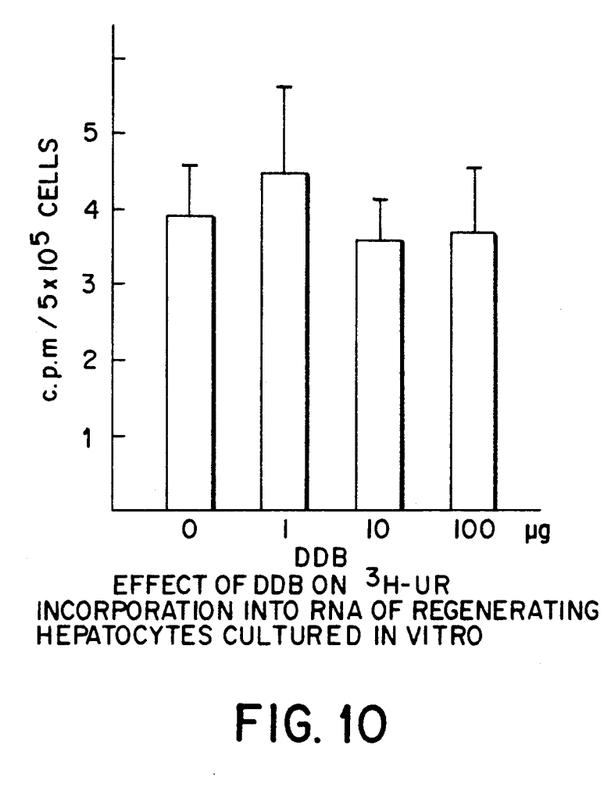
FIG. 10 is a graph of tritiated uridine incorporation in RNA of cultured regenerated rat hepatocytes at various concentrations of DDB.

Male Wistar rats weighing approximately 150 g were partially hepatectomized, approximately 70% of the liver being removed. The abdomens were sutured and the animals were maintained for 5 days on a diet of laboratory chow and water ad lib. The animals were sacrificed and the livers excised, perfused with collagenase solution and the hepatocytes isolated by the method of Seglen. The hepatocytes were diluted to $5 \times 10^5$ ml in RPMI-1640 medium and divided into 4 groups. To each 1 ml of hepatocytes was added 0, 1, 10 or 100 μg of DDB in 10 μl of DMSO. After 24 hours, 0.5 μci of tritiated uridine in 10 μl of normal saline was added to the culture medium and the suspension was incubated for an additional 4 hours and treated as in Example 4. The results are shown in FIG. 10.

EXAMPLE 12

Figure 11:
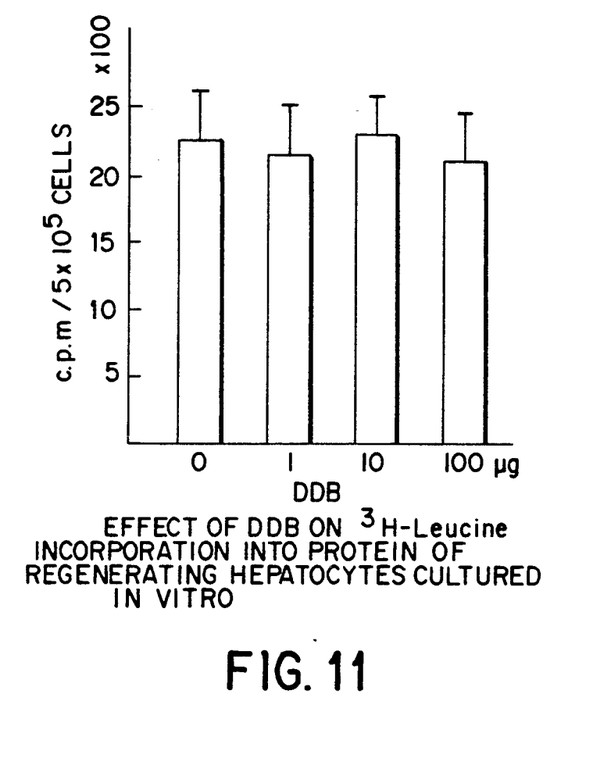
FIG. 11 is a graph of tritiated leucine incorporation in the protein of cultured regenerated rat hepatocytes at various concentrations of DDB.

Male Wistar rats weighing approximately of 150 g were partially hepatectomized, approximately 70% of the liver being removed. The abdomens were sutured and the animals were maintained for 5 days on a diet of laboratory chow and water ad lib. The animals were sacrificed and the livers excised, perfused with collagenase solution and the hepatocytes isolated by the method of Seglen. The hepatocytes were diluted to $5 \times 10^5$ ml in RPMI-1640 medium and divided into 4 groups. To each 1 ml of hepatocytes was added 0, 1, 10 or 100 μg of DDB in 10 μl of DMSO. After 24 hours, 0.5 μci of tritiated leucine in 10 μl of normal saline was added to the culture medium and the suspension was incubated for an additional 4 hours. The protein was isolated and incorporation of tritiated leucine measured as described in Example 6. The results are shown in FIG. 11.

EXAMPLE 13

Figure 12:
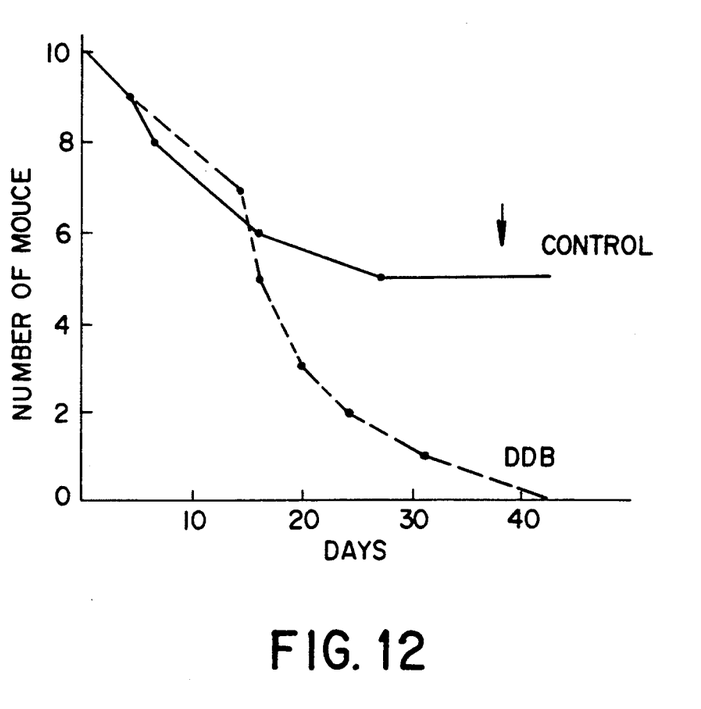
FIG. 12 is a graph showing the survival time of mice implanted with murine ascitic hepatoma cells in the presence of 6-mercaptopurine and in the presence of both DDB and 6-mercaptopurine.

Two groups of 10, male, Kumin strain mice weighing 18-22 g were inoculated i.p., with 0.2 ml of murine ascitic hepatoma cells obtained from transplanted mice after dilution 2 fold. To the first group, was administered 48 mg/kg of 6-mercaptopurine, i.p., daily. To the second group, in addition to the same amount of 6-MP, was administered 300 mg/kg of DDB by intubation. At the end of 42 days, all of the mice treated with 6-MP alone had died, while 6 of the mice treated with both DDB and 6-MP survived. The results are shown in FIG. 12.

EXAMPLE 14

Murine ascitic hepatoma cells at a concentration of $5 \times 10^5$ cell/ml were cultured in RPMI-1640 medium in a 5% $CO_2$ incubator in the presence of 10 μg of DDB or 10 μg of methotrexate or 10 μg of DDB plus 10 μg of methotrexate. DDB was dissolved in DMSO. Methotrexate was dissolved in distilled water. A control containing an equal volume of DMSO and distilled water was also used. After 24 hours of culture, 0.5 μci of tritiated thymidine was added to each sample and culturing continued for an additional 4 hours. The cells were treated and incorporation of tritiated thymidine into DNA was measured by the procedure described in Example 4. The results are shown in Table 2.

TABLE 2

Effect of DDB combining with MTX on cell proliferation and $^3$H-TdR incorporation into DNA of ascitic hepatoma in vitro.

$n = 6, \overline{X} \pm S.D.$

| Treatment | Cell number × 10$^5$/ml | c.p.m./10$^5$ cells |
|---|---|---|
| DMSO 10 μl + D.W. 10 μl | 7.75 ± 1.14 | 4917 ± 1391 |
| DDB 10 μl + D.W. 10 μl | 6.48 ± 0.31* | 2054 ± 776** |
| DMSO 10 μl + MTX 10 μg | 5.84 ± 0.35** | 366 ± 139*** |
| DDB 10 μl + MTX 10 μg | 5.58 ± 0.68** | 230 ± 101*** |

DDB dissolved in DMSO, MTX dissolved in D.W. (distilled water)
*p < 0.05
**p < 0.01
***p < 0.001

EXAMPLE 15

Using the method of Example 13, except that 6-MP was substituted for methotrexate, the DNA uptake of tritiated thymidine in murine ascitic hepatoma cells was measured. The results are shown in Table 3.

TABLE 2

Effect of DDB combining with 6-MP on cell proliferation and $^3$H-TdR incorporation into DNA of ascitic hepatoma in vitro.

$n = 6, \overline{X} \pm S.D.$

| Treatment | Cell number × 10$^5$/ml | c.p.m./10$^5$ cells |
|---|---|---|
| DMSO 10 μl + D.W. 10 μl | 7.75 ± 1.06 | 3403 ± 565 |
| DDB 10 μl + D.W. 10 μl | 6.10 ± 0.65** | 1010 ± 224*** |
| DMSO 10 μl + 6-MP 10 μg | 5.81 ± 0.45** | 1500 + 481*** |
| DDB 10 μl + 6-MP 10 μg | 4.94 ± 1.22** | 554 ± 262*** |

DDB dissolved in DMSO, 6-MP dissolved in D.W. (distilled water)
**p < 0.01
***p < 0.001

We claim:

1. A method for the treatment of BEL-7402 human hepatocarcinoma which comprises administering to a mammal in need of such treatment a composition comprising about 6 parts by weight of dimethyl 4,4'-dimethoxy-5,6,5',6'-dimethylene-dioxybiphenyl-2,2'-dicarboxylate to 1 part by weight of 6-mercaptopurine in an amount effective to inhibit growth of said hepatocarcinoma.

2. A method according to claim 1, wherein the amount of dimethyl 4,4'-dimethoxy-5,6,5',6'-dimethylene-dioxybiphenyl-2,2'-dicarboxylate administered is about 1.25 to 350 mg per kg of body weight of said mammal per day.

3. A pharmaceutical composition comprising about 6 parts of dimethyl 4,4'-dimethoxy-5,6,5',6'-dimethylene-dioxybiphenyl-2,2'-dicarboxylate per part of 6-mercaptopurine in an amount effective to inhibit growth of BEL-7402 human heptacocarinoma.

* * * * *